US008501171B2

(12) United States Patent
Bourel et al.

(10) Patent No.: US 8,501,171 B2
(45) Date of Patent: *Aug. 6, 2013

(54) USE OF ADCC-OPTIMIZED ANTIBODIES FOR TREATING WEAK PATIENTS

(75) Inventors: Dominique Bourel, La Madeleine (FR); Sylvie Jorieux, Villeneuve d'Ascq (FR); Christophe De Romeuf, Lambersart (FR); Philippe Klein, Lille (FR); Christine Gaucher, Sequedin (FR); Nicolas Bihoreau, Orsay (FR); Emmanuel Nony, Antony (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 99 days.

This patent is subject to a terminal disclaimer.

(21) Appl. No.: 12/659,824

(22) Filed: Mar. 23, 2010

(65) Prior Publication Data
US 2010/0303826 A1    Dec. 2, 2010

Related U.S. Application Data

(63) Continuation of application No. 10/566,358, filed as application No. PCT/FR2004/002057 on Jul. 30, 2004, now Pat. No. 7,713,524.

(30) Foreign Application Priority Data

Jul. 31, 2003  (FR) ..................... 03 09440

(51) Int. Cl.
    *A61K 39/395*     (2006.01)
(52) U.S. Cl.
    USPC ...................................... 424/130.1
(58) Field of Classification Search
    None
    See application file for complete search history.

(56) References Cited

U.S. PATENT DOCUMENTS

| 7,713,524 B2* | 5/2010 | Bourel et al. ............ 424/130.1 |
| 2002/0098527 A1 | 7/2002 | Shitara et al. |
| 2003/0175969 A1 | 9/2003 | Beliard et al. |
| 2005/0031613 A1* | 2/2005 | Nakamura et al. ......... 424/145.1 |
| 2006/0251652 A1 | 11/2006 | Watkins et al. |

FOREIGN PATENT DOCUMENTS

| EP | 0 576 093 A1 | 12/1993 |
| EP | 1 270 595 B1 | 1/2003 |
| EP | 1 331 266 A1 | 7/2003 |
| EP | 1 443 961 B1 | 8/2004 |
| FR | 03/07067 | * 6/2003 |
| WO | WO 01/77181 A1 | 10/2001 |

OTHER PUBLICATIONS

Ash et al., Annals of Medicine, 2011, 43: 133-141.*
Tsang et al., "B-cell-specific and interferon-γ-inducible regulation of the *HLA-DRα* gene," *Proc. Natl. Acad. Sci.*, Nov. 1988, pp. 8598-8602, vol. 85.
Ohta et al., "Antitumor effects of a novel monoclonal antibody with high binding affinity to ganglioside GD3," *Cancer Immol. Immonother.*, 1993, pp. 260-266, vol. 36, No. 4.
Goto et al., "A novel membrane antigen selectively expressed on terminally differentiated human B cells," *Blood*, 1994, pp. 1922-1930, vol. 84.
Rossman et al., "Variablity in B-cell antigen expression: implications for the treatment of B-cell lymphomas and leukemias with monoclonal antibodies," *The Hematology Journal*, 2001, pp. 300-306, vol. 2.
Niwa et al., "Enhanced natural killer cell binding and activation by low-fucose IgG1 antibody results in potent antibody-dependent cellular cytotoxicity induction at lower antigen density," *Clin. Cancer Res.* Mar. 2005, pp. 2327-2336, vol. 11.
McEarchern et al., "Engineered anti-CD70 antibody with multiple effector functions exhibits in vitro and in vivo antitumor activities," *Blood*, 2007, pp. 1185-1192, vol. 109.
Denardo et al., "Nanomolecular HLA-DR10 antibody mimics: A potent system for molecular targeted therapy and imaging," *Cancer Biother and Radio*, 2008, vol. 23, No. 6. (Abst).
Ishiguro et al., "A defucosylated anti-CD317 antibody exhibited enhanced antibody-dependent cellular cytotocitiy against primary myeloma cells in the presence of effectors from patients," *Cancer Sci.*, Oct. 2010, vol. 101, No. 10.
Horie et al., "CD30: Expression and function in health and disease," *Semin Immunol*, Dec. 1998, pp. 457-470, vol. 10, No. 6. (Abst).
Dorothee et al., "Functional and molecular characterization of a KIR3DL2/p140 expressing tumor-specific cytotoxic T lymphocyte clone infiltrating a human lung carcinoma," *Oncogene*, 2003, pp. 7192-7198, vol. 22.
Hanley et al., "CD44 on LS174T Colon Carcinoma Cells Possesses E-Selectin Ligand Activity," *Can Res*, Jul. 2005, pp. 5812-5817, vol. 65, No. 13.
Robillard et al., "CD33 is expressed on plasma cells of a significant number myeloma patients, and may represent a therapeutic target," *Leukemia*, Sep. 2005, pp. 2021-2022, vol. 19.
Stevenson, G.T., "CD38 as a Therapeutic Target," *Mol Med*, 2006, pp. 346-346, vol. 12.
Loose et al., "Prognostic value of CD25 expression on lymphocytes and tumor cells in squamous-cell carcinoma of the head and neck," *Can Biother and Radio*, Feb. 2008, pp. 25-33, vol. 23, No. 1. (Abst).
Tol et al., "Monoclonal antibodies in the treatment of metastatic colorectal cancer: a review," *Clin Ther*, Mar. 2010, pp. 437-453, vol. 32, No. 3. (Abst).
Advanced Catalogue Search, ATCC No. CRL-1662, Product Description, [online] [retrieved on Sep. 22, 2009]. Retrieved from the Internet: <URL: mhtml:file:// W:\IntellectualProperty\APPLICATIONS\OPPOSITIONS\LFB\atcc crl . . . >.
Advanced Catalogue Search, ATCC No. CRL-1823, Product Description [online] [retrieved on Sep. 22, 2009]. Retrieved from the Internet: <URL: http://www.lgcstandards-atcc.org/LGCAdvancedCatalogueSearch/ProductDescription . . . >.
Armstrong-Fisher et al., "Evaluation of a panel of human monoclonal antibodies to D and Exploration of the synergistic effects of blending IgG1 and IgG3 antibodies on their in vitro biologic function," *Transfusion*, Aug. 1999, pp. 1005-1012, vol. 39.

(Continued)

*Primary Examiner* — Ilia Ouspenski
(74) *Attorney, Agent, or Firm* — Foley & Lardner LLP

(57) ABSTRACT

The invention concerns the use of human or humanized chimeric monoclonal antibodies which are produced in selected cell lines, said antibodies bringing about a high ADCC activity as well as a high secretion of cytokines and interleukins, for treating underpopulations of so-called weak-response patients exhibiting CD16 FCGR3A-158F homozygote or FCGR3A-158V/F heterozygote polymorphism.

10 Claims, 4 Drawing Sheets

OTHER PUBLICATIONS

Figure 1:
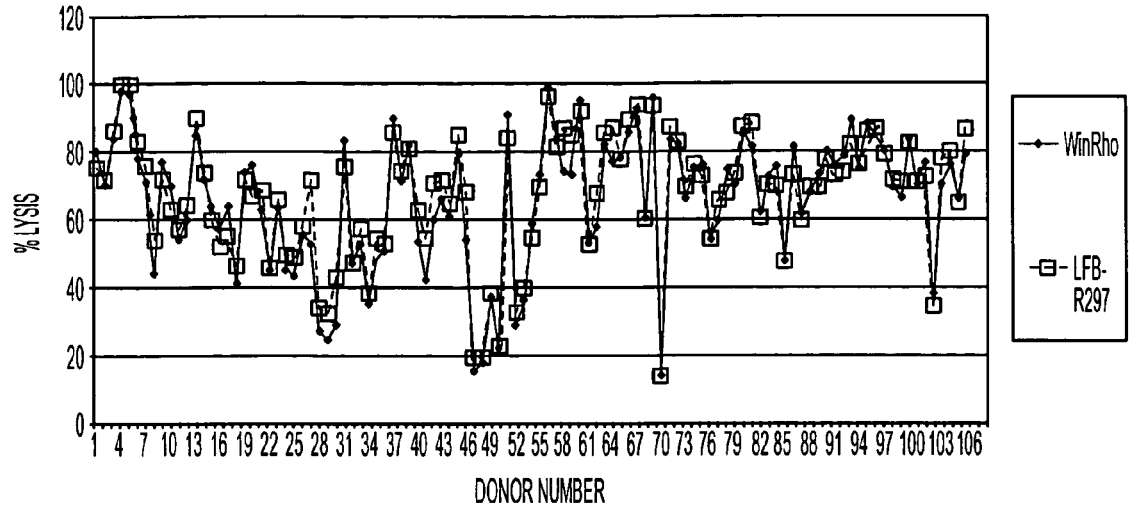

Blood Plasma, Wikipedia, [online] [retrieved on Sep. 22, 2009]. Retrieved from the Internet: <URL: http://en.wikipedia.org/wiki/Blood_plasma>, 3 pages. Revision history of Blood plasma, Wikipedia, [online] [retrieved Sep. 22, 2009]. Retrieved from the Internet: <URL: http://en.wikipedia.org/w/index.php?title=Blood_plasma&limit=500&action=history>, 18 pages.

Boyd et al., "The Effect of the Removal of Sialic Acid, Galactose and Total Carbohydrate on the Functional Activity of Campath-1H," Mole. Immunol., 1995, pp. 1311-1318, vol. 32, Nos. 17/18.

Brand, A., "Immunosuppression and Immunomodulation," Immunological and Infectious Diseases of the Peripheral Nerves, Latov et al., editors, Cambridge University Press, Chapter 24, pp. 366-368, 1998.

Bredius et al., "Role of neutrophile FcγRIIa (CD32) and FcγRIIIb (CD16) polymorphic forms in phagocytosis of human IgG1- and IgG3-opsonized bacteria and erythrocytes," Immunology, 1994, pp. 624-630, vol. 83.

Cant et al., "Glycosylation and functional activity of anti-D secreted by two human lymphoblastoid cell lines," Cytotechnology, 1994, pp. 223-228, vol. 15.

Carroll et al., "Mouse X human heterohybridomas as fusion partners with human," J. Immunol. Methods, 1986, pp. 61-72, vol. 89, Elsevier.

CD61, Wikipedia, [online] [retrieved on Sep. 22, 2009]. Retrieved from the Internet: <URL: http://en.wikipedia.org/wiki/CD61, 5 pages. Revision history of CD61, [online] [retrieved on Sep. 22, 2009]. Retrieved from the Internet: <URL: http://en.wikipedia.org/w/index.php?title=CD61&action=history, 1 page.

Chowdhury et al., "Tailor-made antibody therapeutics," Methods, 2005, pp. 11-24, vol. 36, Elsevier.

Ducrot et al., "Use of the DAF Assay to Assess the Functional Properties of Polyclonal and Monoclonal Rh D Antibodies," Vox Sang, 1996, pp. 30-36, vol. 71.

Galili et al., "A Unique Natural Human IgG Antibody with Anti-α-Galactosyl Specificity," J. Exp. Med., Nov. 1984, pp. 1519-1531, vol. 160.

Goossens, et al., "Human monoclonal antibodies against blood group antigens. Preparation of a series of stable EBV immortalized B clones producing high levels of antibody of different isotypes and specificities," J. Immunol. Methods, 1987, pp. 193-200, vol. 101, Elsevier.

Greenman et al., "Comparative efficiencies of bispecific F(ab'γ)$_2$ and chimeric mouse/human IgG antibodies in recruiting cellular effectors for cytotoxicity via Fcγ receptors," Cancer Immunol. Immunother., 1992, pp. 361-369, vol. 34.

Hadley et al., "The functional activity of FcγRII and FcγRIII on subsets of human lymphocytes," Immunology, 1992, pp. 446-451, vol. 76.

Hsu et al., "Differential N-Glycan Patterns of Secreted and Intracellular IgG Produced in Trichoplusia ni Cells," J. Biol. Chem., Apr. 1997, pp. 9062-9070, vol. 272, No. 14.

Hughes-Jones et al., "Nucleotide sequences and three-dimensional modeling of the $V_H$ and $V_L$ domains of two human monoclonal antibodies specific for the D antigen of the human Rh-blood-group system," Biochem. J., 1990, pp. 135-140, vol. 268.

Ip et al., "Structural Characterization of the N-Glycans of a Humanized Anti-CD18 Murine Immunoglobulin G," Archives of Biochemistry and Biophysics, Feb. 1991, pp. 387-399, vol. 208, No. 2.

Jefferis et al., "IgG-Fc-mediated effector functions: molecular definition of interaction sites for effector ligands and the role of glycosylation," Immunol. Reviews, 1998, pp. 59-76, vol. 163.

Keler et al., "Bispecific antibody-dependent Cellular Cytotoxicity of HER2/neu-overexpressing Tumor Cells by Fcγ Receptor Type I-expressing Effector Cells," Cancer Research, Sep. 1997, pp. 4008-4014, vol. 57.

Kilmartin et al., "Rat Monoclonal Antitubulin antibodies Derived by Using a New Nonsecreting Rat Cell Line," J. Cell Biol., Jun. 1982, pp. 576-582, vol. 93.

Klein et al., "Human recombinant anti-Rh(D) monoclonal antibodies: Improvement of biological properties by in vitro class-switch," Human Antibodies, 1997, pp. 17-25, vol. 8, No. 1.

Kumpel et al., "Activity and Fcγ receptor utilization of IgG anti-D monoclonal antibodies in monocytes chemiluminescence assays and lymphocyte ADCC assays," 4th Workshop on Mabs against human red blood cells and related antigens, Paris, Jul. 19-20, 2002, p. 1.

Kumpel et al., "Galactosylation of human IgG monoclonal anti-D produced by EBV-transformed By-lymphoblastoid cell lines is dependent on culture method and affects Fc receptor-mediated functional activity," Hum. Antibod. Hybridomas, 1994, pp. 143-151, vol. 5. Nos. 3 and 4.

Kumpel et al., Heterogeneity in the ability of IgG1 monoclonal anti-D to promote lymphocyte-mediated red cell lysis, Eur. J. Immunol., 1989, pp. 2283-2288, vol. 19.

Kumpel et al., "Human Rh D monoclonal antibodies (BRAD-3 and BRAD-5) cause accelerated clearance of Rh D+ red blood cells and suppression of Rh D immunication in Rh D− volunteers," Blood, 1995, pp. 1701-1709, vol. 86, American Society of Hematology.

Kumpel, B.M., "Efficacy of RhD monoclonal antibodies in clinical trials as replacement therapy for prophylactic anti-D immunoglobulin: more questions than answers," Vox Sang., 2007, pp. 99-111, vol. 93.

Kumpel, B.M., "Monoclonal anti-D for prophylaxis of RhD haemolytic disease of the newborn," Transfus. Clin. Biol., 1997, pp. 351-356, vol. 4.

Lifely et al., "Glycosylation and biological activity of CAMPATH-1H expressed in different cell lines and grown under different culture conditions," Glycobiology, 1995, pp. 813-822, vol. 5, No. 8.

Lund et al., "Control of IgG/Fc Glycosylation: A Comparison of Oligosaccharides from Chimeric Human/Mouse and Mouse Subclass Immunoglobulin Gs," Mole. Immunol., 1993, pp. 741-748, vol. 30, No. 8.

Melamed et al., "Requirements for the establishment of heterohybridomas secreting monoclonal human antibody to rhesus (D) blood group antigen," J. Immunol. Methods, 1987, pp. 245-251, vol. 104, Elsevier.

Merriam-Webster, Webster's Third New International Dictionary of the English Language Unabridged, 1961, p. 1761.

Mori et al., "Non-fucosylated therapeutic antibodies: the next generation of therapeutic antibodies," Cytotechnology, 2007, pp. 109-114, vol. 55.

Nakamura et al., "Chimeric Anti-Ganglioside $G_{M2}$ Antibody with Antitumor Activity," Cancer Research, Mar. 1994, pp. 1511-1516, vol. 54.

Papac et al., "A high-throughput microscale method to release N-linked oligosaccharides from glycoproteins for matrix-assisted laser desorption/ionization time-of-flight mass spectrometric analysis," 1998, pp. 463-472, vol. 8, No. 5.

Paterson et al., "Variation in IgG1 heavy chain allotype does not contribute to differences in biological activity of two human anti-Rhesus (D) monoclonal antibodies," Immunotechnology, 1998, pp. 37-47, vol. 4, Elsevier.

Presta, Leonard G., "Engineering of therapeutic antibodies to minimize immunogenicity and optimize function," Advanced Drug Delivery Reviews, 2006, pp. 640-656, vol. 58, Elsevier.

Puthalakath et al., "Glycosylation Defect in Lec1 Chinese Hamster Ovary Mutant is Due to a Point Mutation in N-Acetylglucosaminyltransferase I Gene," J. Biol. Chem., Nov. 1996, pp. 27818-27822, vol. 271, No. 44.

Raju et al., "Species-specific variation in glycosylation of IgG: evidence for the species-specific sialylation and branch-specific galactosylation and importance for engineering recombinant glycoprotein therapeutics," Glycobiology, 2000, pp. 477-486, vol. 10, No. 5.

Revillard, Jean-Pierre, Immunologie, 2d Ed., 1995, various chapters, DeBoeck Université.

Rothman et al., "Antibody-dependent Cytotoxicity Mediated by Natural Killer Cells is Enhanced by Castanospermine-induced Alterations of IgG Glycosylation," Mole. Immunol., 1989, pp. 1113-1123, vol. 26, No. 12.

Segal et al., "The Role of Non-immune IgG in Controlling IgG-Mediated Effector Functions," Mole. Immunol., 1983, pp. 1177-1189, vol. 20, No. 11.

Shaw et al., "Human Lymphocyte, Monocyte, and Neutrophil Antibody-Dependent Cell-Mediated Cytotoxicity toward Human Erythrocytes," Cell. Immunol., 1978, pp. 122-133, vol. 41.

Shields et al., "Lack of Fucose on Human IgG1 N-Linked Oligosaccharide Improves Binding to Human FcγRIII and Antibody-dependent Cellular Toxicity," *J. Bio. Chem.*, Jul. 2002, pp. 26733-26740, vol. 277, No. 30.

Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *J. Biol. Chem.*, Jan. 2003, pp. 3466-3473, vol. 278, No. 5.

Shitara et al., "A new vector for the high level expression of chimeric antibodies in myeloma cells," *J. Immunol. Methods*, 1994, pp. 271-278, vol. 167, Elsevier Science B.V.

Sibéril et al., "Selection of a human anti-RhD monoclonal antibody for therapeutic use: Impact of IgG glycosylatiion on activating and inhibitory FcγR functions," *Clinical Immunol.*, 2006, pp. 170-179, vol. 118, Elsevier.

Takahashi et al., "Comparative Structural Study of the N-Linked Oligosaccharides of Human IgG Normal and Pathological Immunoglobulin G," *Biochemistry*, 1987, pp. 1137-1144, vol. 26.

Tandai et al., "Structural Study of the Sugar Moieties of Monoclonal Antibodies Secreted by Human-Mouse Hybridoma," *Archives of Biochemistry and Biophysics*, Dec. 1991, pp. 339-348, vol. 291, No. 2.

Teillaud, Jean-Luc, "Engineering of monoclonal antibodies and antibody-based fusion proteins: successes and challenges," *Expert Opin. Biol. Ther.*, 2005, pp. S15-S27, vol. 5, Suppl. 1, Ashley Publications.

Umaña et al., "Engineered glycoforms of an antineuro-blastoma IgG1 with optimized antibody-dependent cellular cytotoxic activity," *Nature Biotechnology*, Feb. 1999, pp. 176-180, vol. 17.

Urbaniak et al., "Prediction of the Outcome of Rhesus Haemolytic Disease of the Newborn: Additional Information Using an ADCC Assay," *Vox Sang.*, 1984, pp. 323-329, vol. 46.

Urbaniak, S.J., "ADCC (K-Cell) Lysis of Human Erythrocytes Sensitized with Rhesus Alloantibodies," *British J. Haematology*, 1979, pp. 303-314, vol. 42.

Wright et al., Effect of Altered $C_H2$-associated Carbohydrate Structure on the Functional Properties and in Vivo Fate of Chimeric Mouse-Human Immunoglobulin G1, J. Exp. Med., Sep. 1994, pp. 1087-1096, vol. 180, The Rockefeller University Press.

Wright et al., "Effect of C2-Associated Carbohydrate Structure on Ig Effector Function: Studies with Chimeric Mouse-Human IgG1 Antibodies in Glycosylation Mutants of Chinese Hamster Ovary Cells," *J. of Immunol.*, 1998, pp. 3393-3402.

Wright et al., "Effect of glycosylation on antibody function: implications for genetic engineering," *TIBTECH*, Jan. 1997, pp. 26-32, vol. 15.

Wright et al., "In vivo Trafficking and catabolism of IgG1 antibodies with Fc associated carbohydrates of differing structure," *Glycobiology*, 2000, pp. 1347-1355, vol. 10, No. 12.

Yano et al., "Analysis of N-linked oligosaccharides in the Fc region of an antibody," Experiment Summary, 16 pages, Jun. 23 to Jul. 28, 2009.

B M Kumpel et al., "Clearance of red cells by monoclonal IgG3 anti-D in vivo is affected by the VF polymorphism of FcgammaRIIIa (CD16)", Clinical & Experimental Immunology, vol. 132, No. 1, Apr. 2003, pp. 81-86.

T. Shinkawa et al., "The absence of fucose but not the presence of galactose or bisecting N-acetylglucosamine of human IgG1 complex-type oligosaccharides shows the critical role of enhancing antibody-dependent cellular cytotoxicity", Journal of Biological Chemistry, vol. 278, No. 5, Jan. 31, 2003, pp. 3466-3473.

P. Umana et al., "Engineered Glycoforms of an Antineuroblastoma IGG1 With Optimized Antibody-Dependent Cellular Cytotoxic Activity", Nature Biotechnology, vol. 17, Feb. 1999, pp. 176-180.

Guillaume Cartron et al., "Therapeutic activity of humanized anti-CD20 monoclonal antibody and polymorphism in IgG Fc receptor FcgammaRIIIa gene", Blood, vol. 98, No. 11, Part 1, Nov. 16, 2001, p. 602a.

J.S. Crowe et al., "Humanized Monoclonal Antibody Campath-1H Myeloma Cell Expression of Genomic Constructs Nucleotide Sequence of CDNA Constructs and Comparison of Effector Mechanisms of Myeloma and Chinese Hamster Ovary Cell Derived Material", Clinical and Experimental Immunology, vol. 87, No. 1, 1992, pp. 105-110.

Cartron et al., *Blood*, 2002, 99:754-758.

Notice of Allowance issued on Jan. 15, 2010 by the Examiner in U.S. Appl. No. 10/566,358.

Notice of Allowance issued on Sep. 8, 2009 by the Examiner in U.S. Appl. No. 10/566,358.

Office Action issued on Jul. 1, 2009 by the Examiner in U.S. Appl. No. 10/566,358.

Office Action issued on Mar. 31, 2009 by the Examiner in U.S. Appl. No. 10/566,358.

Office Action issued on Jul. 11, 2008 by the Examiner in U.S. Appl. No. 10/566,358.

Office Action issued on Jan. 24, 2008 by the Examiner in U.S. Appl. No. 10/566,358.

Schlaeth, Martin et al., "Fc-engineered EGF-R antibodies mediate improved antibody-dependent cellular cytotoxicity (ADCC) against KRAS-mutated tumor cells", Cancer Science, May 2010, pp. 1080-1088, vol. 101, No. 5.

Ishiguro, Takahiro et al., "A defucosylated anti-CD317 antibody exhibited enhanced antibody-dependent cellular cytotoxicity against primary myeloma cells in the presence of effectors from patients", Cancer Science, Oct. 2010, pp. 2227-2233, vol. 101, No. 10.

Lewis, T.S. et al., "Distinct apoptotic signaling characteristics of the anti-CD40 monoclonal antibody dacetuzumab and rituximab produce enhanced antitumor activity in non-Hodgkin lymphoma", Clin Cancer Res, Jul. 2011, pp. 4672-4681, vol. 17, Issue, 14. (abstract).

D-Hautcourt, Jean-Luc et al. (contributor), "Quantitative flow cytometric analysis of membrane antigen expression", Current Protocols in Cytometry, 2002, pp. 6.12.1-6.12.22, Supplement 22, John Wiley & Sons, Inc.

Cardarelli, P.M. et al., "Binding to CD20 by anti-B1 antibody or F(ab')(2) is sufficient for induction of apoptosis in B-cell lines", Cancer Immunol Immunother, Mar. 2002, pp. 15-24, vol. 51, Issue 1. (abstract).

Law, Che-Leung et al., "Efficient elimination of B-lineage lymphomas by anti C20-auristatin conjugates", Clin Cancer Res, Dec. 2004, pp. 7842-7851, vol. 10.

Niwa, Rinpei et al., "Enhanced natural killer cell binding and activation by low-fucose IgG1 antibody results in potent antibody-dependent cellular cytotoxicity induction at lower antigen density", Clin Cancer Res, Mar. 2005, pp. 2327-2336, vol. 11.

\* cited by examiner

USE OF ADCC-OPTIMIZED ANTIBODIES FOR TREATING WEAK PATIENTS

This invention relates to the use of humanised or human chimeric monoclonal antibodies with a specific glycosylation having a strong interaction for the CD 16 receptor (FcgammaRIII) of the effector cells of the immune system as well as the property of inducing cytokine and interleukin secretion, for treating populations of patients responding poorly to existing treatments and having a particular polymorphism of their CD16.

Immunotherapy with monoclonal antibodies is becoming one of the most important and innovative strategies in medicine. However, the results obtained in clinical trials appear to be mixed. Indeed, in a number of treatments, the monoclonal antibody does not appear to be active and/or effective enough. Numerous clinical trials have been stopped due to a lack of efficacy and adverse effects incompatible with use as a clinical treatment. These two aspects are closely related, given that relatively inactive and/or ineffective antibodies are administered at high doses to compensate for the lack of efficacy and obtain a therapeutic response. The administration of high doses then causes adverse effects. In addition, it is economically unviable.

These are major problems in the industry of monoclonal antibodies, in particular humanised or human chimeric antibodies. However, these problems are exacerbated for particular populations of patients in whom the therapeutic effect of the antibodies is significantly lower by comparison to the average in the population treated. These patients are commonly called "low-responder patients".

It is known that cell cytotoxicity mediated by antibodies requires binding of the Fab portion of the antibodies to their target as well as an engagement of their Fc domain with the Fc receptors of the effector cells (RFc). On the NK cells, the receptor responsible for this cytotoxicity is CD16.

On the basis this knowledge, studies have been conducted in order to establish a correlation between subpopulations of patients who are refractory (so-called "low-responder" patients) to treatment with an antibody specific to a condition to be treated, and CD16 polymorphism.

In a study of 2000 (Cartron G, Dacheux L, Salles G, Solal-Celigny P, Bardos P, Colombat P, Watier H, Therapeutic activity of humanized anti-CD20 monoclonal antibody and polymorphism in IgG Fc receptor FcgammaRIIIa gene, Blood. 2002 Feb. 1; 99(3): 754-8), the composition of the population of patients treated with Rituxan® was analysed according to the CD16 polymorphism in position 158. It was composed of 20% FCGR3A-158V homozygotes (patients homozygous for valine in position 158 of CD16), 35% FCGR3A-158F homozygotes (patients homozygous for phenylalanine in position 158 of CD16) and 45% FCGR3A-158V/F heterozygotes (patients heterozygous for valine/phenylalanine in position 158 of CD16). The ADCC activity as well as the clinical efficacy of the anti-CD20 Rituxan® antibodies are correlated with the CD16 polymorphism: the FCGR3A-158F homozygous or FCGR3A-158V/F heterozygous patients are less responsive to the Rituxan® treatment than FCGR3A-158V homozygous patients.

Thus, this study made it possible to demonstrate that the differences in response to treatments with therapeutic antibodies are associated with a CD16 polymorphism.

However, this study does not propose a solution for reducing the effect of this polymorphism in so-called "low-responder" patients treated with therapeutic antibodies. It does not provide a therapeutic treatment suitable for the treatment of low-responder patients.

In addition, other results have been obtained from clinical studies performed with anti-Rhesus antibodies, which have shown that the elimination of Rhesus positive erythrocytes by IgG3 anti-D was faster in FCGR3A-158F homozygous patients (Kumpel B M, De Haas M, Koene H R, Van De Winkel J G, Goodrick M J. Clearance of red cells by monoclonal IgG3 anti-D in vivo is affected by the VF polymorphism of Fcgamma RIIIa (CD16). Clin Exp Immunol. 2003 April; 132(1): 81-6). However, the low number of patients studied does not enable a technical result to be drawn from this study.

The objective of the present invention is to provide antibodies effective for treating patients in whom treatments with the'antibodies currently available fail, or suffering from adverse effects.

The applicant has found that antibodies in which the Fc domain has a particular glycan structure with a cytotoxic activity particularly suitable for the treatment of so-called "low-responder" patients, which is not affected by the FCGR3A-158F homozygous or FCGR3A-158V/F polymorphism of amino acid 158 of CD16, unlike the antibodies produced in CHO of which the cytotoxic activity is affected by this polymorphism. In addition, the applicant has found that the antibodies according to the invention cause cytokine/chemokine production, which also contributes to the reinforcement of the therapeutic effect by stimulating effector mechanisms of the immune system in the patients treated.

The invention therefore proposes the use of antibodies according to the invention in the treatment of sub-populations of so-called "low-responder" patients. These antibodies have an ADCC activity and a cytokine and/or chemokine production up to 100 times greater than the antibodies available in current treatments.

Thus, the invention relates to the use of an optimised humanised or human chimeric monoclonal antibody, characterised in that:
a) it is produced in a cell line selected for its properties of glycosylation of the Fc region of an antibody, or
b) the glycan structure of the Fc region was modified ex vivo, and/or
c) its primary sequence was modified so as to increase its interaction with the Fc receptors;
wherein said antibody has (i) an ADCC level via CD16 (FcgammaRIIIA) above 60%, 70%, 80% or preferably above 90% compared with the same antibody produced in a CHO line or a homologous antibody available on the market, for the preparation of a drug intended for treating conditions in patients with the polymorphism of the homozygous FCGR3A-158V/F or FCGR3A-158F CD16 receptor and considered "low-responders" to treatments with the antibodies currently available.

For the purposes of the invention, the term "low-responder" patients refers to patients with a 20% to 50% reduction in the response to treatments with therapeutic antibodies by comparison with so-called "high-responder" patients, i.e. patients with a complete response corresponding to the disappearance of all, measurable clinical signs and symptoms of the disease.

For example, in the case of a study of the clearance of erythrocytes or of another cell type in the bloodstream, the term "low-responder" patients refers to patients who have a significantly longer clearance by comparison with another group of patient's. In the treatment of leukaemia, the following are differentiated:
the high responders with a complete response corresponding to the disappearance of all measurable signs and symptoms of the disease, with respect to the clinical exam and the biological laboratory data and radiographic exams. The reduction in the size of the largest tumours is greater than 75%.

patients who respond partially are described in the article Cheson B D et al, Report of an international workshop to standardize response criteria for non-Hodgkin's lymphomas. NCI Sponsored International Working Group. J Clin Oncol. 1999 April; 17(4): 1244. Review. Erratum in: J Clin Oncol 2000 June; 18(11): 2351.

low-responders, corresponding to patients having a so-called stable condition, with at least 50% reduction of the tumour mass, less than 25% increase in lesions and no new lesions. This group of patients also includes patients in whom no response is observed (progression of disease progressing to death).

Thus, for a subpopulation of so-called "low-responder" patients; in relation to the polymorphism of amino acid 158 of CD16 (homozygous FCGR3A-158F or FCGR3A-158V/F) or another polymorphism associated with this CD16 polymorphism, the efficacy of the treatment is better with the optimised antibodies of the invention, and comes close to that of so-called "high-responder" patients.

Indeed, the interaction of the receptor for the Fc of antibodies is different according to the CD16 polymorphisms (aa158), as the homozygous FCGR3A-158V phenotype has a better affinity than the homozygous FCGR3A-158F and heterozygous FCGR3A-158V/F form. The antibodies according to the invention have a strong interaction with CD16, which may explain the fact that their functional activity is not or is only very slightly affected by the homozygous FCGR3A-158F or FCGR3A-158V/F CD16 polymorphism.

The invention therefore addresses a particular population of patients with a CD16 polymorphism (homozygous FCGR3A-158F or FCGR3A-158V/F), in particular patients in whom the treatment with the antibodies currently available has failed and/or patients suffering from adverse effects justifying the administration of the optimised antibody of the invention.

The conditions treated with the antibody according to the invention are not limited to particular conditions, but include all conditions capable of being treated with monoclonal antibodies.

In addition to the very significant improvement in the CD16-type ADCC activity (FcγRIIIA), the antibody of the invention can be characterised in that it induces the secretion of at least one cytokine by a type of effector cell of the immune system expressing the CD16 receptor more than 50%, 100% or preferably more than 200% with respect to the same antibody produced in a CHO line or compared with a homologous antibody available on the market. The type of cytokine is selected from IL-1, IL-4, IL-12, IL-18, IL-21, IL-2, IL-3, IL-5, IL-6, IL-7, IL-8, IL-9, IL-10, IFNα, IFNβ, TNFα, TGFβ, IP10 and TNF, IFNγ.

In the context of the invention, we show that antibodies having a strong interaction with CD16 have the advantage of inducing the production of cytokines, or chemokines, in particular the production of IFNγ. The two aforementioned characteristics complement one another. Indeed, the production of IFNγ or other cytokines or chemokines, by effector cells, induced by the antibodies according to the invention, can reinforce the therapeutic effect by stimulating effector mechanisms of the immune system in the patients treated. The mechanism of action of such a stimulation corresponds in particular to a positive autocrine regulation of the effector cells. The antibodies binding to CD16 induce a cytotoxic activity as well as the production of IFNγ or other cytokines/chemokines, which, in the end, results in a further increase in the cytotoxic activity.

Preferably, this antibody has an ADCC level above at least 100% compared to the same antibody produced in a CHO line or a homologous antibody available on the market, and a level of production, of at least one cytokine by a type of effector cell of the immune system expressing the CD16 receptor, greater than at least 100% with respect to the same antibody produced in a CHO line or a homologous antibody available on the market.

The cytokines of which the release is caused by optimised antibodies are selected from interleukins, cytokines, chemokines, interferons and tumour necrosis factors (TNF).

Thus, the antibody according to the invention is capable of inducing the secretion of at least one type of cytokine selected from IL-1, IL-4, IL-12, IL-18, IL-21, IL-2, IL-3, IL-5, IL-6, IL-7, IL-8, IL-9, IL-10, IFNα, IFNβ, TNFα, TGFβ, IP10 and TNF, IFNγ, by the effector cells of the immune system.

Preferably, the antibody selected has the capacity to induce the secretion of IFNγ or other cytokines/chemokines by the effector cells of the immune system expressing the CD16 receptor or more specifically IL2 by the CD16 Jurkat cell. The level of IFNγ or other cytokines and/or chemokines secreted expresses the capacity for interaction of the Fc region of the antibody with CD16 and also expresses its capacity for binding to the antigen. The secretion of IFNγ or other cytokines and/or chemokines by the cells of the immune system can increase and/or induce the cytotoxic activity of the effector cells (NK, monocytes, macrophage, polynuclear neutrophils, etc).

The effector cells can express an endogenous CD16 possibly modulable by cytokines and/or chemokines or growth factors or be transformed. The term transformed cell refers to a cell genetically modified so as to express a receptor, in particular the CD16 receptor.

In a particular embodiment, the antibody of the invention is capable of inducing the secretion of at least one cytokine by a leukocyte, in particular the family of NK (Natural Killer) cells, or by cells of the myelomonocyte line (monocytes-macrophages and dendrite cell).

Preferably, for the selection of antibodies, a Jurkat line transfected with an expression vector encoding the CD16 receptor as the effector cell is used. This line is particularly advantageous because it is immortalised and is maintained in culture indefinitely. The level of IL2 secreted expresses the capacity for interaction of the Fc region of the antibody with CD16 and also expresses its capacity for binding to the antigen.

Various Jurkat lines transfected with an expression vector encoding the CD16 receptor can be used as an effector cell, which lines each express a particular CD16.

In addition, the optimised antibody can be prepared after having been purified and/or modified ex vivo with regard to the glycan structure of its Fc region. To this end, any chemical, chromatographic or enzymatic means appropriate for modifying the glycan structure of the antibody can be used. For example, it is possible to purify antibodies obtained from various sources, to add one or more glycosyl transferase(s), in particular a galactosyl-transferase, to a reaction mixture, and to incubate for a predetermined time until antibodies with the glycan structure described above are obtained.

The selection can be made of antibodies produced by cells commonly used to produce therapeutic antibodies, such as rat myeloma lines, in particular YB2/0 and its derivatives, human lymphoblastoid cells, insect cells, murine myeloma cells, hybridomas as well as eukaryotic cells such as, for example, yeast.

It is also possible to produce the antibodies in a genetically modified mammal cell line, for example genetically modified CHO, by introducing one or more sequence(s) expressing one or more glycosyl transferase(s), in particular selected from an enzyme involved in the modification of oligosaccharide chains in position 1 of the fucose alpha bonded to position 6 of the N-acetylglucosamine residue at the reductive end, in particular a 1,6-fucosyltransferase, and a galactosyl-transferase. The selection can also be applied to the evaluation of antibodies produced by transgenic plants or transgenic mammals.

Therefore, the production in CHO serves as a reference (CHO being used in the production of drug antibodies) for comparing and selecting the production systems leading to the antibodies according to the invention. A comparison with polyclonal antibodies can also be useful in monoclonal antibody efficacy tests. Thus, for a subpopulation of so-called "low-responder" patients in relation to the polymorphism of amino acid 158 of CD16 or another polymorphism associated with this polymorphism, the efficacy of the treatment is better with the optimised antibodies of the invention, and is similar to that of so-called "high-responder" patients. We show that the functional activity of the optimised monoclonal antibodies is related to that of therapeutic polyclonal antibodies. Thus, in some therapeutic trials, the polyclonal antibodies can be used as controls in tests on the efficacy of monoclonal antibodies of different origins. This makes it possible to select monoclonal antibodies intended for the treatment of subpopulations of low-responder patients.

Thus, in some therapeutic trials, the polyclonal antibodies can be used as controls in tests on the efficacy of monoclonal antibodies of different origins. This makes it possible to select monoclonal antibodies intended for the treatment of subpopulations of low-responder patients. Another alternative consists of performing a comparison with the antibodies available on the market, in particular antibodies being developed, antibodies for which marketing authorisation has been obtained, or antibodies for which the clinical trials were stopped, and shown to be ineffective or to produce adverse effects at the doses administered. Indeed, the modified antibodies of the invention are at least 100% more effective for activating the ADCC supported by effector cells of the immune system, which means lower administration doses than those used for the antibodies mentioned above, and, in this case, the possibility of treating patients in whom the antibodies currently available have proved to be ineffective.

In a preferred embodiment of the invention, the antibody can, in a first step, be selected for its capacity of interaction with the CD16 receptor, then tested and selected as described above for its properties of inducing the production of a cytokine, in particular IL-2, by the Jurkat CD16 cells or IFNγ by the effector cells expressing CD16.

Such antibodies have this dual property of inducing ADCC via the CD16 and of inducing the production of IFNγ or other cytokines and/or chemokines by the cells of the immune system can increase and/or induce the cytotoxic activity of the effector cells (in particular, NK, monocytes, macrophage, and polynuclear neutrophils).

Thus, the invention relates to the use of the antibody defined above for the preparation of a drug intended for the treatment of conditions in patients homozygous for phenylalanine in position 158 of CD16 (FCGR3A-158F homozygotes) or patients heterozygous for valine/phenylalanine in position 158 of CD16 (FCGR3A-158V/F).

Such antibodies according to the invention have a specific glycosylation. The antibodies according to the invention have a biantennary-type Fc domain, with short chains, low sialylation, non-intercalating terminal mannoses and GlcNAc of the attachment site and low fucosylation.

Thus, in another embodiment of the invention relates to the use of a humanised or human chimeric monoclonal antibody of which the glycan structure of the Fc domain of the antibody corresponds to a biantennary type, with short chains, low sialylation, non-intercalating terminal mannoses and GlcNAc of the attachment site, and low fucosylation for the preparation of a drug intended for the treatment of conditions in patients homozygous for phenylalanine in position 158 of CD16 (FCGR3A-158F homozygotes) or patients heterozygous for valine/phenylalanine in position 158 of CD16 (FCGR3A-158V/F).

Indeed, this glycan form of the Fc domain of the antibody confers on the latter the properties of inducing a strong DCC and the production of cytokines and/or chemokines as described above.

In this antibody, the level of intercalary GlcNac is non-zero. For example, compositions with a concentration over 60%, preferably over 80% for the forms G0+G1+G0F+G1F, can be used given that the concentration in forms G0F+G1F is lower than 50%, preferably lower than 30% for the preparation of a drug intended for the treatment of patients homozygous for phenylalanine in position 158 of CD16 (FCGR3A-158F homozygotes) or patients heterozygous for valine/phenylalanine in position 158 of CD16 (FCGR3A-158V/F).

The antibodies mentioned above are preferably IgG1.

Another objective of the invention is to provide a therapeutic treatment method including the administration of a humanised or human chimeric monoclonal antibody of which the glycan structure of the Fc domain of the antibody corresponds to a biantennary type, with short chains, low sialylation, non-intercalating terminal mannoses and GlcNAc of the attachment site and low 2.5 fucosylation, to patients homozygous for phenylalanine in position 158 of CD16 (FCGR3A-158F homozygotes) or patients heterozygous for valine/phenylalanine in position 158 of CD16 (FCGR3A-158V/F).

The patients are advantageously homozygous for phenylalanine in position 158 of CD16 (FCGR3A-158F homozygotes).

Preferably, in the patients treated, the antibodies currently available resulted in therapeutic failure or the patients experienced adverse effects.

The dose of the antibody administered to the patient is preferably 2 times, 5 times, and preferably 10 times, 25 times, 50 times or most preferably 100 times lower than a dose indicated with an antibody having the same specificity but different glycosylation or produced in a CHO line.

The dose of the antibody administered to the patient is advantageously between 2 and 5 times, between 5 and 10 times, between 5 and 25 times, between 5 and 50 times or preferably between 5 and 100 times lower than a dose of an antibody with the same specificity by different glycosylation or produced in a CHO line.

In another embodiment of the invention, the antibody of the invention can be produced in rat myeloma cell lines, for example YB 2/0 (ATCC no. CRL 1662). Indeed, such cells enable a glycosylated antibody as previously described to be obtained. Thus, in a complementary embodiment of the invention relates to the use of a humanised or human chimeric monoclonal antibody produced in a rat myeloma line, for example YB2/0 or one of its derivatives, for the preparation of a drug intended for the treatment of patients having the homozygous form FCGR3A-158V/F or FCGR3A-158F of CD16, in particular patients in whom treatment with the antibodies currently available has failed, or suffering from adverse effects justifying the administration of the optimised antibody of the invention. The invention preferably relates to the use of antibodies produced in rat myeloma cell lines, in particular YB2/0 and its derivatives. Said antibodies having the dual property of inducing, via the homozygous form FCGR3A-158V/F or FCGR3A-158F of CD16, ADCC, as well as the production of IFNγ or other cytokines and/or chemokines by the cells of the immune system, which is capable of increasing and/or inducing the cytotoxic activity of effector cells (NK, monocytes, macrophage, polynuclear neutrophils, etc.) described as expressing the CD16 receptor, are used for the preparation of a drug intended for the treatment of a particular population of low-responder patients or patients in whom the treatment with the antibodies currently available has failed or suffering from adverse effects.

The antibody according to the invention, produced in rat myeloma lines, in particular YB2/0 or one of its derivatives, has the glycan structure of the fragment Fc as described above, the concentration in forms G0+G1+G0F+G1F and G0F+G1F as described above, and it induces a cytotoxicity by ADCC and the secretion of cytokines in the way described above.

The antibody of the invention can be directed against a non-ubiquitous antigen present in healthy donor cells (for example, the antibody is of anti-Rhesus human erythrocyte specificity), or an antigen of a pathological cell or an pathogenic organism for humans, in particular against an antigen of a cancer cell or a cell infected by a virus. It is advantageous to use the antibodies defined above for the treatment of cancers and infections by pathogenic agents for these patients.

The conditions requiring the administration of such antibodies in these patients include, for example, diseases selected from haemolytic disease of the newborn and those escaping the immune response, in particular Sezary syndrome, chronic myeloid leukaemias, chronic lymphoid leukaemias (CLL-B), solid tumours, breast cancer, conditions related to the environment in particular affecting people exposed to polychlorinated biphenyls, infectious diseases, in particular tuberculosis, chronic fatigue syndrome (CFS), parasitic infections such as, for example, schistosomas or paludism, in particular in pregnant women, and viral infections for targeting the virus reservoir cells (HIV, HCV, HBV in particular) and the infected cells.

The conditions treated include conditions in which the antigen is poorly expressed (Rhesus D antigen on erythrocytes leukaemia, chronic lymphoid leukaemia B (CLL-B), for example). "Poorly-expressed antigen" refers to a number of antigenic sites below 250,000, preferably below 100,000 or 50,000 and very advantageously below 10,000 or 5,000 per target cell.

In a particular embodiment of the invention addresses patients with the homozygous FCGR3A-158V/F or FCGR3A-158V form of CD16 and having CLL-B. As the CD20 is very poorly expressed on these tumour cells, the use of anti-CD20 antibodies according to the invention for treating these patients is particularly advantageous.

The cancers concern most specifically cancers of HLA class-II positive cells, B-cell lymphomas, B-cell acute leukaemias, Burkitt's lymphoma, Hodgkin's lymphoma, myeloid leukaemias, chronic lymphoid leukaemias (CLL-B), T-cell lymphomas and leukaemias, non-Hodgkin's lymphomas and chronic myeloid leukaemias.

The antibody according to the invention can be an anti-HLA-DR antibody or an anti-CD20.

In a particular embodiment of the invention, when the antibody is an anti-CD20, the antibody is advantageously administered at a dose below 187.5 mg/kg, at 75 mg/kg, at 37.5 mg/kg, 15 mg/kg, 7.5 mg/kg or preferably below 3.75 mg/kg. The dose administered is advantageously between 187.5 mg/kg and 75 mg/kg, or between 75 mg/kg and 37.5 mg/kg, between 75 mg/kg and 15 mg/kg, between 75 mg/kg and 7.5 mg/kg and preferably between 75 mg/kg and 3.75 mg/kg or between 15 mg/kg and 3.75 mg/kg.

This antibody advantageously has an ADCC level above 100% and an IL-2 production level by the CD16 Jurkat cell up to 1000% greater than that of Rituxan®.

The anti-CD20 of the invention can be produced in a rat myeloma line, in particular YB2/0.

In addition, by way of example, the antibodies according to the invention can be second generation antibodies corresponding to the antibodies currently available, listed in Table 1.

TABLE 1

| Name and brand name of the antibody | Company | target | indication |
|---|---|---|---|
| Edrecolomab PANOREX | Centocor | anti Ep-CAM | colorectal cancer |
| Rituximab RITUXAN | Idec Licensed to Genentech/ Hoffman la roche | anti CD20 | B cell lymphoma thrombocytopenia purpura |
| Trastuzumab HERCEPTIN | Genentech Licensed to Hoffman la roche/ Immunogen | anti HER2 | ovarian cancer |
| Palivizumab SYNAGIS | Medimmune Licensed to Abbott | | RSV |
| Alemtuzumab CAMPATH | BTG Licensed to Schering | anti CD52 | leukaemia |
| ibritumomab tiuxetan ZEVALIN | IDEC Licensed to Schering | anti CD20 | NHL |
| Cetuximab IMC-C225 | Merck/BMS/ Imclone | anti HER1 | cancers |
| Bevacizumab AVASTIN | Genentech/ Hoffman la roche | anti VEGF | Lung, colorectal, kidney cancers |
| Epratuzumab | Immumedics/Amgen | anti CD22 | cancers: non- |

TABLE 1-continued

| Name and brand name of the antibody | Company | target | indication |
|---|---|---|---|
| Hu M195Mab | Protein Design Labs | ND | Hodgkin's lymphoma cancers |
| MDX-210 | Medarex/Immuno-Designed Molecules | Bispecific HER2Neu/CD64 | Breast, ovarian, prostate cancers |
| BEC2 Mitumomab | Imclone | anti GD3 | Small cell lung carcinoma |
| Oregovomab OVAREX | Altarex | anti CA125 | Ovarian cancer |
| Ecromeximab KW-2971 | Kyowa-Hakko | anti GD | malignant melanoma |
| ABX-EGF | Abgenix | EGF | cancers |
| MDX010 | Medarex | ND | cancers |
| XTL 002 | XTL biopharmaceuticals | ND | anti-viral: HCV |
| H11 SCFV | viventia biotech | ND | cancers |
| 4B5 | viventia biotech | anti GD2 | cancers |
| XTL 001 | XTL biopharmaceuticals | ND | anti-viral: HBV |
| MDX-070 | MEDAREX | Anti-PSMA | Prostate cancer |
| TNX-901 | TANOX | anti CD-23 | |
| IDEC-114 | IDEC | Protein C inhibition | non-Hodgkin's lymphoma |

Other antibodies can be selected from anti Ep-CAM, anti HER2, anti CD52, anti HER1, anti GD3, anti CAl25, anti GD, anti GD2, anti CD-23 and anti Protein C; anti-KIR3DL2, anti-EGFR, anti-CD25, anti-CD38, anti-CD30, anti-CD33, anti-CD44, inhibitor-specific anti-idiotypes, for example, coagulation factors, and anti-virals: HIV, HBV, HCV and RSV.

In a preferred embodiment the antibody is an anti-HLA-DR. This antibody has an ADCC level above 100% and a level of production of IL2 by the CD16 Jurkat cell, or IFNγ by an effector cell of the immune system expressing the CD16 receptor of up to 1000 compared with the same antibody expressed in the CHO line, the expression line of Remitogen®.

The anti-HLA-DR of the invention can be produced in a rat myeloma line, in particular YB2/0.

The invention also relates to the use of an antibody described above for the production of a drug intended to induce the expression of IL-1, IL-4, IL-12, IL-18, IL-21, IL-2, IL-3, IL-5, IL-6, IL-7, IL-8, IL-9, IL-10, IFNα, IFNβ, TNFα, TGFβ, IP10 and IFNγ by the natural effector cells of the immune system, which drug is useful in particular in the treatment of cancer and infections in patients in whom the antibodies currently available have failed, or suffering from adverse effects justifying the administration of the optimised antibody of the invention, and in particular having the form V/F158 or F/F158 of CD16.

Other embodiments and advantages of the invention will be described in the following examples, which should be considered to be illustrative and do not limit the scope of the invention.

LEGENDS OF THE FIGURES

FIG. 1: ADCC activity of the anti-Rhesus D monoclonal antibody R297 (IgG1 T125 produced in YB2/0) and polyclonal antibodies WinRho in the presence of effector cells (PBMC: Peripheral Blood Mononuclear Cells) of different blood donors and polyvalent immunoglobulins (Tegeline 500 μg/ml).

Figure 2:
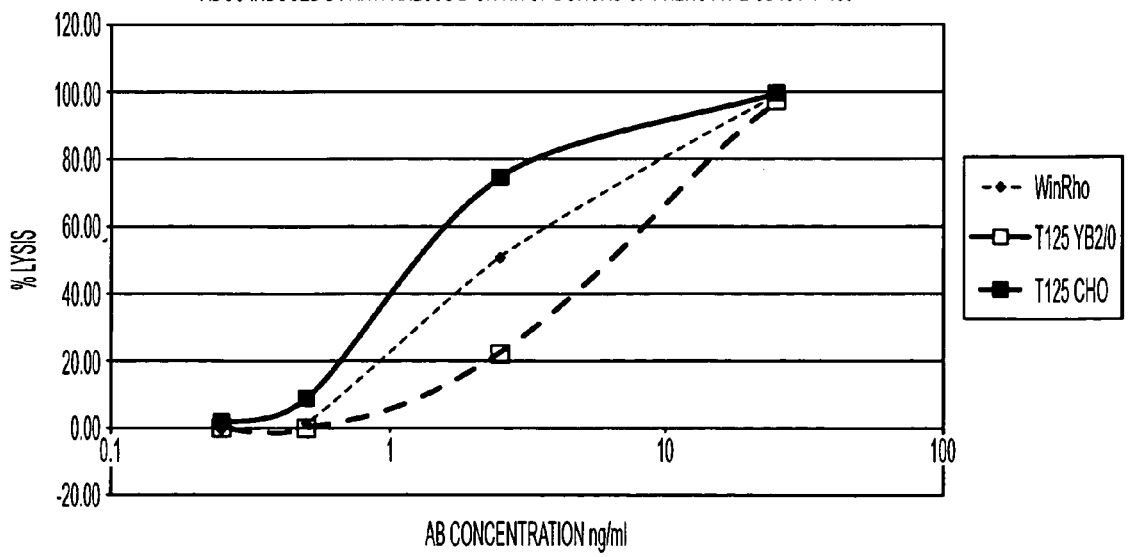

FIG. 2: ADCC induced by anti-Rhesus D antibodies (polyclonal antibodies WinRho, T125 produced in YB2/0 and T125 produced in CHO) on NK cells of donors of homozygous phenotype CD16 FCGR3A-158F.

Figure 3:
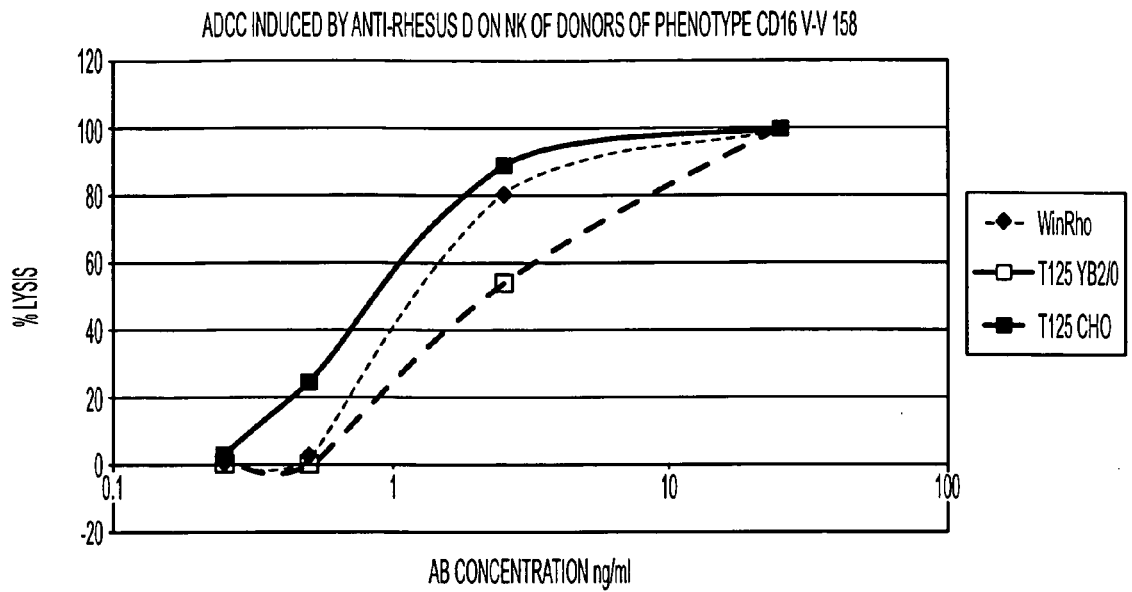

FIG. 3: ADCC induced by anti-Rhesus D antibodies (polyclonal antibodies WinRho, T125 produced in YB2/0 and T125 produced in CHO) on NK cells of donors of homozygous phenotype CD16 FCGR3A-158F.

Figure 4:
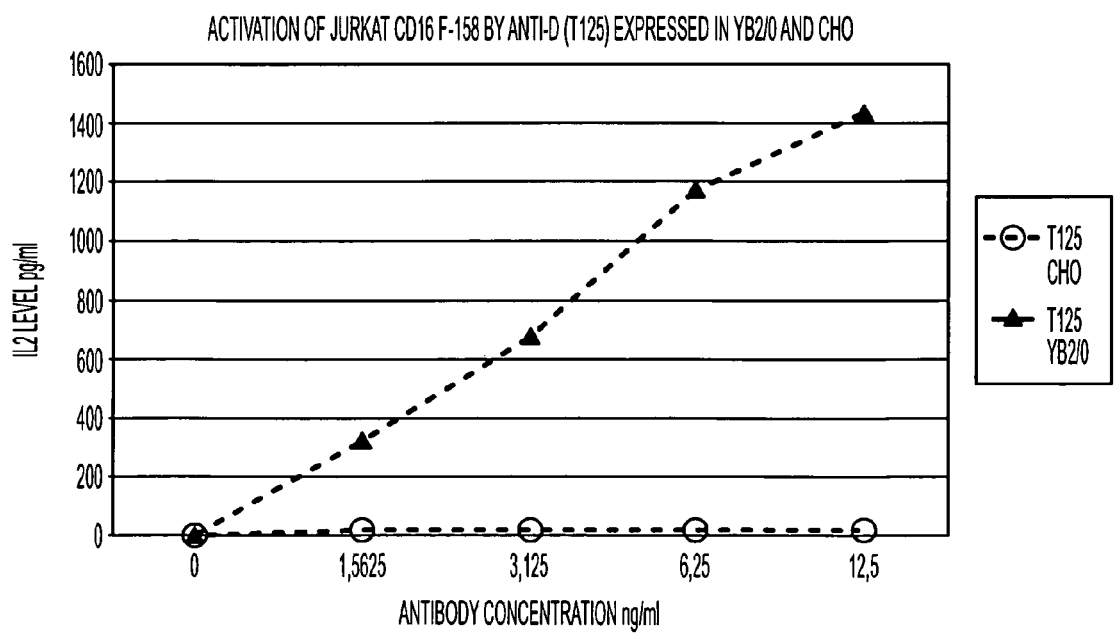

FIG. 4: Activation of homozygous FCGR3A-158F CD16 Jurkat by the anti-Rhesus D antibodies T125 expressed in YB2/0 and CHO.

Figure 5:
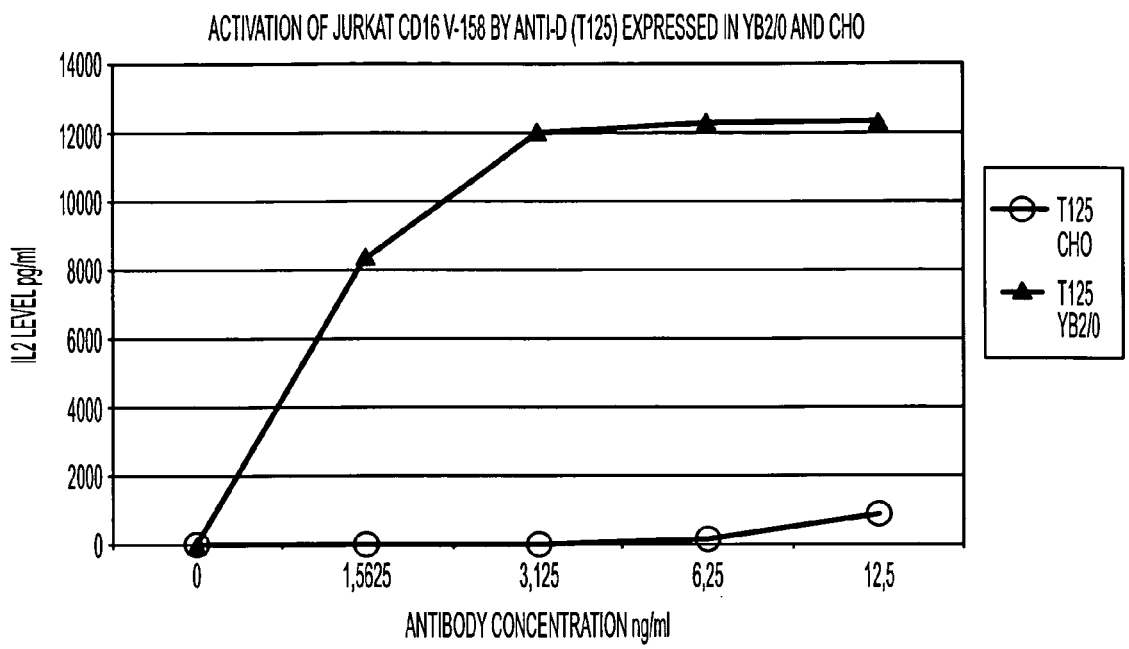

FIG. 5: Activation of homozygous FCGR3A-158V CD16 Jurkat by the anti-Rhesus D antibodies T125 expressed in YB2/0 and CHO.

Figure 6:
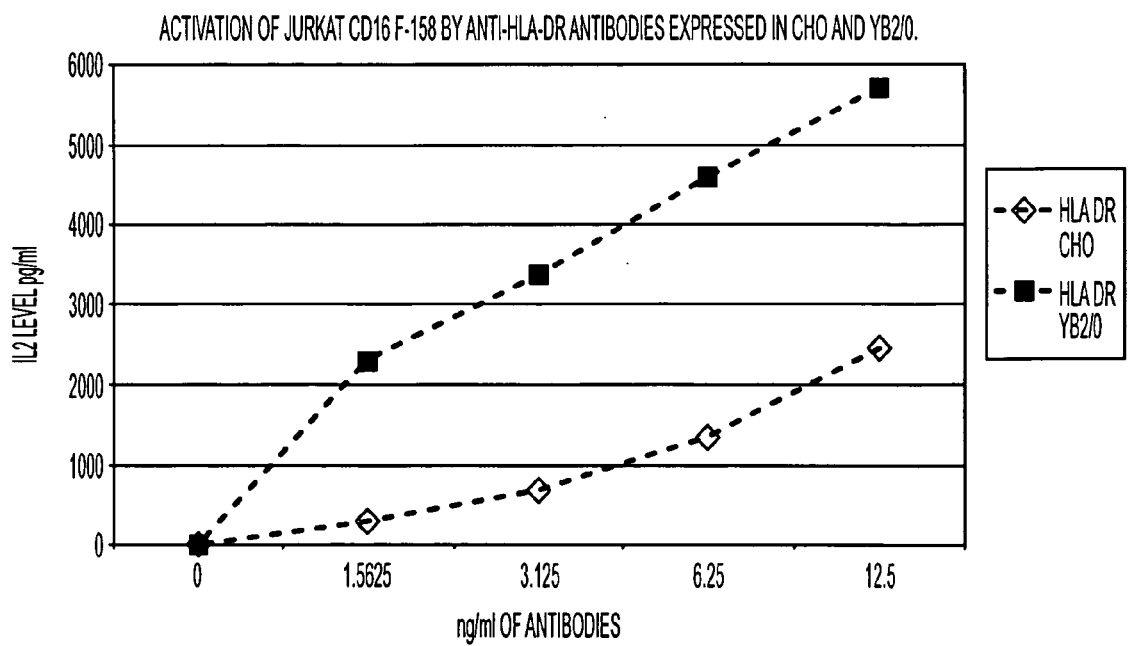

FIG. 6: Activation of homozygous FCGR3A-158F CD16 Jurkat induced by the anti-HLA-DR antibodies expressed in YB2/0 and CHO.

Figure 7:
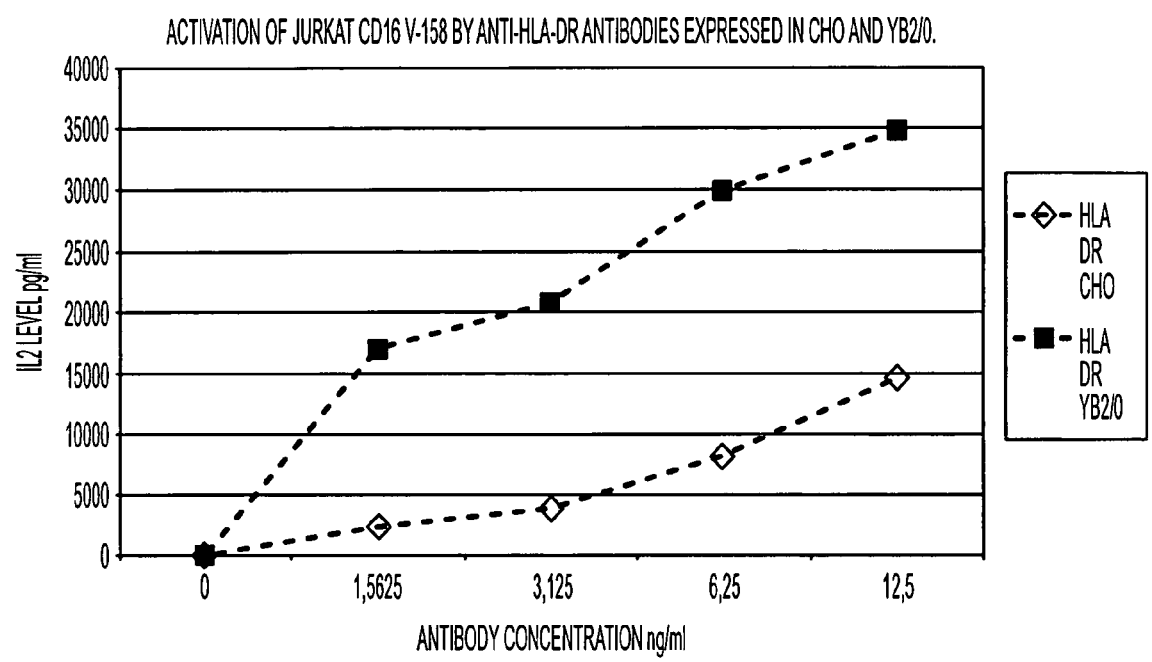

FIG. 7: Activation of homozygous FCGR3A-158V CD16 Jurkat induced by the anti-HLA-DR antibodies expressed in YB2/0 and CHO.

EXAMPLES

Example 1

ADCC Activity of the Anti-Rhesus D Monoclonal Antibody 8297 Compared with the Polyclonal Anti-D Antibodies on a Group of 107 Blood Donors The respective capacities of the anti-Rhesus D R 297 monoclonal antibody and polyclonal anti-D antibodies to lyse erythrocytes in the presence of effector cells of different individual donors are compared (FIG. 1).

The effector cells come from a group of 107 blood donors. The mononuclear cells (PBMC) are isolated from a blood bag by centrifugation on a Ficoll gradient (Pack Plus Pharmacia). The platelets are removed by centrifugation (190 g, 15 min) and the residual red blood cells are lysed with NH4Cl. The cells are washed and resuspended at $8 \times 10^7$ cells/ml in IMDM.

The red blood cells obtained from therapeutic concentrates (group O, Rhesus +) are treated for 10 min with papain (1 mg/ml) then washed three times in a saline buffer and adjusted to a concentration of $4\times10^7$/ml or $2\times10^7$/ml (NK test) in IMDM.

The test is performed in a plate with 96 wells (NUNC). The culture supernatants or the purified antibodies (100 µl to 200 ng/ml in IMDM+0.5% FBS), the effector cells (25 µl), the red blood cells (25 µl) and the polyvalent immunoglobulins (Tegeline, LFB) (50 µl) are incubated for 16 h at 37° C. in a CO2-enriched atmosphere. For the non-specific lysis, the effector cells are replaced with IMDM. After 16 h at 37° C., the plates are centrifuged. 60 µl of supernatants are collected and mixed with 60 µl of 2.7 diaminofluorene (DAF, Sigma).

After 5 min, the OD is measured at 620 nm.

The percentage of lysis is estimated by using a calibration curve obtained with different dilutions of red blood cells lysed with NH4Cl, corresponding to 100%, 75%, 50%, 25% and 0% lysis, respectively.

On the basis of the genotypic study conducted on donors of the same geographic region, the present study estimates that the average distribution of the 107 donors with regard to the CD16 polymorphism is 27 FCGR3A-158F homozygotes, 20 FCGR3A-158V homozygotes and 60 FCGR3A-158V/F.

The results show a wide variability in the capacity of the effector cells of the different subjects to induce lysis of the positive Rhesus erythrocytes, regardless of the antibodies tested. The antibodies expressed in the YB2/0 cell line have a cytolytic activity comparable to that of the polyclonal antibodies, regardless of the donor studied, and consequently regardless of the CD16 polymorphism of the effector cells of the donor (see FIG. 1).

Example 2

ADCC Efficacy of the Antibodies Produced in CHO and YB2/0 According to the CD16 Polymorphism The same sequence encoding a specific IgG1 of the Rhesus D antigen was transfected into CHO and YB2/0 cell lines. The antibodies were incubated with positive Rhesus erythrocytes (target cells) and NK cells from 6 different donors (3 FCGR3A-158V homozygotes and 3 FCGR3A-158F homozygotes) previously genotyped for their CD16 phenotype in position 158. The NK cells are isolated using the magnetic bead separation technique (MACS) of Myltenyi. The NK cells are washed and resuspended at $2\times10^7$/ml and/or $6\times10^7$/ml in IMDM. The red blood cells are adjusted to a concentration of $2\times10^7$/ml in IMDM. The Tegeline is replaced by the IMDM. Aside from these modifications, the test is identical to the ADCC test with PBMC.

The cytotoxic activity of the antibodies on the erythrocytes (ADCC) was evaluated (FIG. 2 and FIG. 3).

The antibody produced in the CHO line induced a lower lysis than the antibody produced in YB2/0, regardless of the donor's phenotype. The R297 antibody expressed in the YB2/0 line induced, from the lowest concentrations, a stronger cytolytic activity. At the maximum concentration of 25 ng/ml, the two antibodies induced the same percentage of ADCC.

At concentrations below 25 ng/ml, the difference in lysis between the antibody produced in CHO and that produced in YB2/0 is greater in the homozygous FCGR3A-158F donors than in the homozygous FCGR3A-158V donors. At a concentration of 2.5 ng/ml, in the presence of homozygous FCGR3A-158V NK cells, the antibody produced by CHO induced 54% lysis while that produced by YB2/0 induced 89% lysis, that is, a 56% increase. By contrast, at the same concentration, in the presence of homozygous FCGR3A-158F NK cells, the antibody produced by CHO induced only 22% lysis while that produced by YB2/0 induced 74% lysis, that is a 236% increase.

The antibody expressed in the YB2/0 line therefore proved to be a better product for treating the patients giving a low lysis with the antibodies produced in CHO. Thus, the difference in ADCC activity between the FCGR3A-158V and homozygous FCGR3A-158F patients is lower with the antibody expressed in YB2/0 (89% and 74%) by comparison with that observed with the antibody expressed in CHO (56% and 22%).

The optimised antibodies have a response that therefore appears to be less dependent on the polymorphic forms of the CD16.

In addition, the monoclonal antibody expressed in YB2/0 always induces a lysis greater than or equal to the polyclonal antibodies.

Example 3

Comparison of the Activation of Homozygous FCGR3A-158F CD16 Jurkat Cells and Homozygous FCGR3A-158F CD16 Jurkat Cells Induced by Anti-Rhesus Antibodies Produced in CHO and YB2/0 Respectively: Evaluation of IL2 Production This test estimates the capacity of the antibodies to bind to the CD16 receptor (Fc gamma RIII) expressed on the CD16 Jurkat cells and to induce the secretion of IL2.

The same sequence encoding an IgG1 (T125) specific to the Rhesus D antigen was transfected into the CHO and YB2/0 cell lines. The antibodies are incubated with positive Rhesus erythrocytes (target cell) and CD16 Jurkat cells (effector cells). Two types of Jurkat cells were used: 1—cells transfected with the gene encoding an RFc bearing the amino acid phenylalanine F in position 158 (form F), 2—cells transfected with the gene encoding an RFc bearing the amino acid valine V in position 158 (form V). The amount of cytokine (IL2) secreted by the CD16 Jurkat cells was measured by ELISA.

In a 96-well plate in mixture: Antibody: 50 µl of a dilution of 50; 37.5; 25; 18.75; 12.5; 9.4; 6.25; 3.125 ng/ml in IMDM (Iscove's Modified Dulbecco's) Medium 5% FBS (foetal bovine serum)

PMA 50 µl of a dilution at 40 ng/ml in IMDM 5% FBS

Red blood cells treated with papain. 50 µl at $8\times10^6$/ml in IMDM 5% FBS

Jurkat CD16. 50 µl at $2\times10^6$/ml in IMDM 5% FBS

Incubation 1 night at 37° C.

Then centrifugation of plates, collection of 100 µl of supernatants and assay of IL2 with the commercial kit (Quantikine of R/D). Reading at 450 nm.

The antibody expressed in the YB2/0 line is capable of inducing a higher secretion of IL2, contrary to the antibody expressed in CHO, regardless of the CD16 phenotype (FIGS. 4 and 5).

The antibody produced in CHO does not induce the secretion of IL2 from homozygous FCGR3A-158F CD16 Jurkat and only a very small production of IL2 with the homozygous FCGR3A-158V form.

As one of the special features of the Rhesus system is the low expression of the antigen at the membrane surface, it appears that under these conditions, the antibody expressed in the YB2/0 line is a much better product for activating the effector cells with the homozygous form FCGR3A-158F of CD16 which do not appear to be capable of being activated with the antibody produced in CHO. As regards the homozygous form FCGR3A-158V, very small amounts of antibodies produced by YB2/0 (<1.56) make it possible to induce an activation comparable to that obtained with higher concentrations of antibodies produced in CHO (12.5 ng/ml).

With the homozygous form FCGR3A-158F and at a concentration of 12.5 ng/ml, the antibody produced in CHO induces a secretion of IL2 (18 pg/ml) lower than 2% of that induced by the antibody produced in YB2/0 (1435 µg/ml). This corresponds to an increase of more than 7000%, when the antibody produced in YB2/0 is used, by comparison with the antibody produced in CHO.

With the homozygous form FCGR3A-158V and at a concentration of 12.5 ng/ml, the antibody produced in CHO induces a secretion of IL2 (869 pg/ml) lower than 8% of that induced by the antibody produced in YB2/0 (12312 pg/ml). This corresponds to an increase of more than 1300%, when the antibody produced in YB2/0 is used, by comparison with the antibody produced in CHO.

Example 4

Comparison of the Activation of Homozygous FCGR3A-158F CD16 Jurkat Cells and Homozygous FCGR3A-158V Jurkat Cells Induced by Two Anti-HLA-Dr Antibodies Expressed in CHO and YB2/0, Respectively: Evaluation of the Secretion of IL2.

The same sequence encoding an IgG1 specific to the HLA-DR antigen was transfected into the CHO and YB2/0 cell lines. The antibodies are incubated with Raji cells (positive HLA-DR target cell) and CD16 Jurkat cells (effector cells). Two types of Jurkat cells were used: 1-cells transfected with the gene encoding an RFc bearing the amino acid phenylalanine F in position 158 (form F), 2—cells transfected with the gene encoding an RFc having the amino acid valine V in position 158 (form V). The quantity of cytokines (IL2) secreted by the CD16 Jurkat cells was measured by ELISA. In 96-well plates in mixture:
Antibody: 50 µl of a dilution of 50; 37.5; 25; 18.75; 12.5; 9.4; 6.25; 3.125 ng/ml in IMDM 5% FBS
PMA 50 µl of a dilution at 40 ng/ml in IMDM 5% FBS
Raji cells: 50 µl at $6 \times 10^5$/ml in IMDM 5% FBS
Jurkat CD16. 50 µl at $20 \times 10^6$/ml in IMDM 5% FBS Incubation 1 night at 37° C.
Then centrifugation of plates, collection of 100 µl of supernatants and assay of IL2 with the commercial kit (Quantikine of R/D). Reading at 450 nm.

The antibody expressed in the YB2/0 line is capable of inducing a higher secretion of IL2, contrary to the antibody expressed in CHO, regardless of the CD16 phenotype (FIGS. 6 and 7).

Unlike the Rhesus system on erythrocytes, the expression of the HLA-DR antigen at the membrane surface of the Raji cell is not low (200,000 to 400,000 copies). Under these conditions, it appears that the antibody expressed in the YB2/0 line is a much better product for activating the effector cells with the form F158 as well as V158 of CD16, and more specifically with low antibody concentrations. Thus, the concentration of 1.56 ng/ml, the antibody produced in CHO induces a secretion of IL2 (2410 pg/ml) lower than 15% of that induced by the antibody produced in YB2/0 (16952 pg/ml). This corresponds to an increase of more than 600% when the antibody produced in YB2/0 by comparison with the antibody produced in CHO.

At a concentration of 12.5 ng/ml, the antibody produced in CHO induces a secretion of IL2 (14597 pg/ml) lower than 45% of that induced by the antibody produced in YB2/0 (34823 pg/ml). This corresponds to an increase of more than 100% when the antibody produced in YB2/0 is used, by comparison with the antibody produced in CHO.

The antibody expressed in the YB2/0 line is therefore a much better product for inducing the secretion of cytokines of effector cells with the polymorphic form V158 (FCGR3A-158V homozygotes) and F158 (FCGR3A-158F homozygotes).

The invention claimed is:

1. A method for treating a cancer or an infection by a pathogenic agent, comprising:
administering a composition of antibodies to a patient in need thereof,
wherein said antibodies are specific to an antigen expressed by the cancer or infection to be treated in the patient,
wherein the cancer or infection has a number of antigenic sites below 250,000 per target cell, and
wherein said antibodies are over 60%, for the forms G0+G1+G0F+G1F, given that the forms G0F+G1F are lower than 50%, and
wherein said antibodies are selected from the group consisting of anti-HLA-DR, anti-CD20, anti Ep-CAM, anti HER2, anti CD52, anti HER1, anti GD3, anti CA125, anti GD, anti GD2, anti CD-23 and anti Protein C, anti-KIR3DL2, anti-EGFR, anti-CD25, anti-CD38, anti-CD30, anti-CD33, and anti-CD44.

2. The method according to claim 1, wherein said patient is homozygous for phenylalanine in position 158 of CD16 (FCGR3A-158F homozygotes) or said patient is heterozygous for valine/phenylalanine in position 158 of CD16 (FCGR3A-158V/F).

3. The method according to claim 1, wherein the number of antigenic sites is below 100,000 per target cell.

4. The method according to claim 3, wherein the number of antigenic sites is below 50,000 per target cell.

5. The method according to claim 3, wherein the number of antigenic sites is below 10,000 per target cell.

6. The method according to claim 1, wherein the dose of said antibody administered to the patient is between 2 and 100 times lower than a dose of an antibody of the same specificity but of different glycosylation or produced in a CHO line.

7. The method according to claim 6, wherein the dose of said antibody administered to the patient is between 5 and 25 times lower than a dose of an antibody of the same specificity but of different glycosylation or produced in a CHO line.

8. The method according to claim 1, wherein the antibody is directed against an antigen of a cancer cell or of an organism pathogenic for humans.

9. The method according to claim 1, wherein the antibody is anti-HLA-DR.

10. The method according to claim 1, wherein the antibody is anti-CD20.

* * * * *